(12) United States Patent
Lloyd

(10) Patent No.: US 6,879,397 B2
(45) Date of Patent: Apr. 12, 2005

(54) LIGHT SCATTERING DETECTOR

(75) Inventor: Jack Lloyd, Panama City, FL (US)

(73) Assignee: The United States of America as represented by the Secretary of the Navy, Washington, DC (US)

(*) Notice: Subject to any disclaimer, the term of this patent is extended or adjusted under 35 U.S.C. 154(b) by 447 days.

(21) Appl. No.: 09/950,240

(22) Filed: Sep. 7, 2001

(65) Prior Publication Data
US 2003/0048451 A1 Mar. 13, 2003

(51) Int. Cl.[7] .................. G01N 21/49; G01N 21/01
(52) U.S. Cl. .................. 356/336; 356/343; 356/246
(58) Field of Search .................. 356/336, 343, 356/246

(56) References Cited

U.S. PATENT DOCUMENTS 4,882,478 A * 11/1989 Hayashi et al. ............ 356/343
5,185,641 A * 2/1993 Igushi et al. ............... 356/336
5,936,729 A * 8/1999 Igushi ....................... 356/336

* cited by examiner

Primary Examiner—Richard A. Rosenberger
(74) Attorney, Agent, or Firm—Donald G. Peck; Harvey A. Gilbert

(57) ABSTRACT

An apparatus and method permits measuring of near-direct forward scattering functions in water to enable acceptable underwater imaging for detection, classification, and identification of objects, such as mines. A source of light mounted on a housing member receiving ambient water emits a beam of light along an axis to a scattering detector assembly mounted on the base member. The detector assembly has a central active region disposed in the axis to receive portions of the light beam emitted along the axis and a plurality of concentric active regions are located radially outwardly from the central active region and the axis to receive scattered portions of the light beam. The central and concentric active regions provide signals representative of the magnitudes of the axial and scattered portions of the light beam for determination of the scattering function of the ambient water.

21 Claims, 1 Drawing Sheet

LIGHT SCATTERING DETECTOR

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

This invention relates to an apparatus for measuring light scattering. More particularly, this invention measures near direct-forward scattering function of light in water for underwater imaging.

Currently there is renewed interest in developing electro-optic sensors for underwater imaging used in the detection, classification, and identification of a number of submerged objects, such as mines. The performance of these sensors is strongly influenced by the characteristics of the water in which they are operated. For acceptable imaging one of the most influential environmental parameters which affects the performance is scattering. In particular, the parameter, or function of near-direct forward scattering that is attributed to the water medium and dissolved and particulate matter in the water medium dominates the ability to resolve fine details of images.

Historically, this scattering function has been difficult to measure, and no available sensors are known to accurately perform this measurement. In fact, direct measurement of the scattering phase function has not been attempted often. The report, "*Volume Scattering Functions for Selected Ocean Waters*" by Scripps Institution of Oceanography for Naval Air Development Center, October 1972, National Technical Information Service AD-753 474, is the only known published account of direct measurements available. The device of the Scripps report used a movable detector that could be positioned over essentially the full arc from the direction the beam was emitted to the direction the beam was directly reflected (0–180 degrees relative to the direction of the emitted beam). The arc the movable detector traveled was large, making it acceptable for effective real-time scientific measurements; however, the device was not suitable for general use at work sites in the ocean.

Indirect measurements of other phenomena in the water have been made on occasion in the form of Modulation Transfer Functions (MTFs) and Point Spread Functions (PSFs). But these measurements are not directly relatable to the underlying scattering function, as they provide a measurement of integrated effects from which the scattering function cannot be extracted.

Thus, in accordance with this inventive concept, a need has been recognized in the state of the art for a detector apparatus deployable in the ocean to measure near-direct forward scattering of ambient water.

SUMMARY OF THE INVENTION

The present invention provides an apparatus for and method of measuring near-direct forward scattering in water. A source of light is mounted on a housing member to emit a beam of light along an axis of emission and a scattering detector assembly is mounted on the housing member a predetermined distance from the light source. The detector assembly has a central active region disposed in the axis to receive portions of the light beam emitted along the axis, and a plurality of concentric active regions located radially outwardly from the central active region and the axis to receive scattered portions of the light beam. The central active region and the concentric active regions provide signals representative of magnitudes of the axial portions and scattered portions of the light beam.

An object of the invention is to provide an apparatus for and method of measuring near-direct forward scattering in water.

Another object of the invention is to provide an apparatus for and method of measuring the near-direct forward scattering function in water in the harsh marine environment.

Another object of the invention is to provide an apparatus for and method of measuring near-direct forward scattering in water that is uncomplicated and reliably used in the harsh marine environment Another object of the invention is to provide an apparatus for and method of reliably measuring near-direct forward scattering in the harsh marine environment to permit detection, identification, and classification of submerged objects, such as mines.

Another object of the invention is to provide an apparatus for and method of measuring scattered light in water that can compensate for the progressively, rapidly decreasing magnitude of light scattered outside of the direction of the beam.

Another object is to provide an apparatus for and method of directly comparing received signals to obtain a calibrated return based on known performance of the active areas present to simultaneously obtain the scattering curve in the entire near-forward scattered region.

Another object of the invention is to provide an apparatus for and method of measuring the near-direct forward scattering function in water using a common supply voltage for all active regions of the detector to ensure commonality in the process of optical reception.

Another object of the invention is to provide an apparatus for and method of measuring the near-direct forward scattering function in water having differently shaped and located active regions for detection of optical scattering of light to achieve different measurement goals.

Another object of the invention is to provide an apparatus for and method of measuring the near-direct forward scattering function in water using photo-detecting active mediums like photo-conductive components, photo-diodes.

Another object of the invention is to provide an apparatus for and method of measuring the near-direct forward scattering function in water using one or more avalanche photo diodes to improve strength of signals.

These and other objects of the invention will become more readily apparent from the ensuing specification when taken in conjunction with the appended claims.

DESCRIPTION OF THE PREFERRED EMBODIMENT

Figure 1:
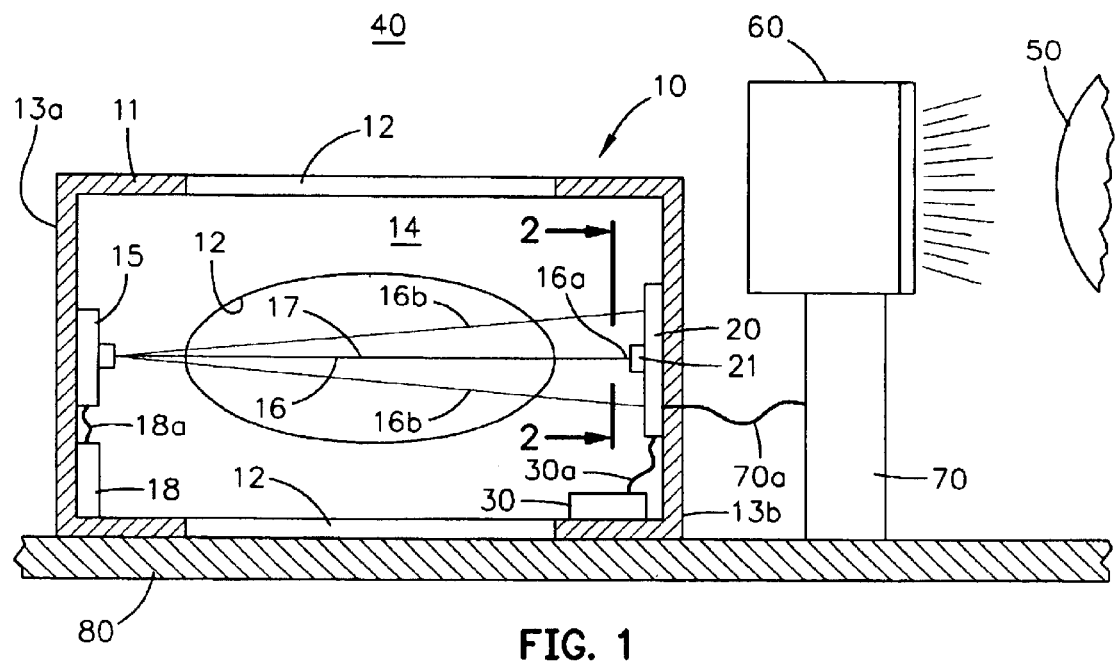
FIG. 1 is a schematic side view of the apparatus of the invention for measuring the near-direct forward scattering function in water in the harsh marine environment.

Referring to FIG. 1, detector 10 of this invention reliably measures the scattering, or scattering function of light. Detector 10 is particularly adapted to measure phenomena known as the near-direct forward scattering function in mediums, such as water 40. Knowing what this scattering function is enables more responsive detection, identification, and classification of objects, such as a mine 50 submerged in the harsh marine environment by a sensor module 60 connected to a processing system 70. The more responsive operation is assured since the performance of sensor module 60 is strongly influenced by the characteristics of the ambient water in which it is operating. Detector 10 of this invention can be compactly packaged and may be mounted adjacent sensor module 60 on a submersible platform 80 or other underwater mounting surface to provide real-time data representative of scattering functions for processing system 70 associated with sensor module 60. Optionally, detector 10 and processing system 70 could be removed from the other constituents and combined to work as a separate Instrument in the ocean to make environmental measurements for a variety of different tasks.

Detector 10 has a rigid can-shaped, or cylindrical shell-shaped housing member 11 provided with a plurality of elongate elliptical openings 12 that extend nearly its length between disc-shaped end caps 13a and 13b. Openings 12 may be shaped differently than elliptical so long as they permit flow of water. Housing member 11 is made from non-corrosive metal or some rigid plastic material to provide structural integrity for the components of detector 10, and elongate elliptical openings 12 in housing member 11 permit substantially unrestricted access to and communication with its interior 14 by ambient water 40. In other words, elliptical openings 12 in housing 11 let water 40 flow freely into and fill interior 14 when detector is immersed in ambient water 40 to quickly permit measurements of scattering.

End cap 13a has a laser 15 secured to it and oriented to emit a beam of light 16 along an axis of emission 17 through interior 14. Light beam 16, having a diameter of about 3 mm for example, is emitted along, or on axis 17 at the proper intensity for a desired measurement of scattering in ambient water 40. A source of power 18 mounted on end cap 13a is connected via leads 18a to laser 15 to maintain the intensity of light beam 16 constant or selectively variable if desired throughout a measurement procedure. Power source 18 could be inside submersible 80 if desired. Light beam 16 is emitted to travel along axis 17 in the direction toward scattering detector assembly 20.

Scattering detector assembly 20 is secured to end cap member 13b at a predetermined distance along axis 17 from laser 15. The exact distance, or separation between laser 15 and scattering detector assembly 20 can range from a few centimeters to meters, or whatever separation is needed to provide accurate measurements in different mediums. Scattering detector assembly 20 of detector 10 receives illumination from laser 15 to measure the near-forward scattering function at a number of angles in the near-forward direction that diverge up to about five degrees from the direction of travel of emitted light beam 16 along axis 17. This degree of angular diversion around light beam 16 is the region of primary interest in determining ability to image fine details underwater.

Figure 2:
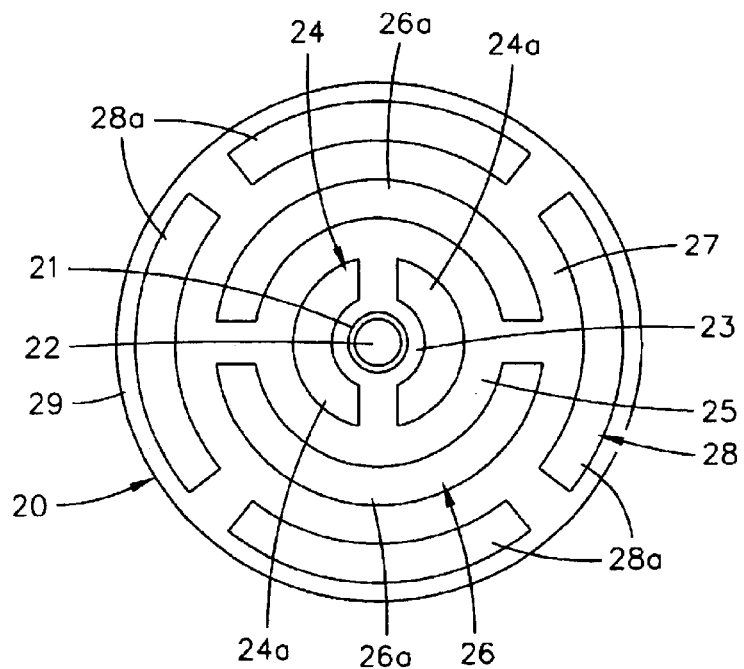
FIG. 2 is a schematic front view of the scatter detector assembly taken generally along lines 2—2 in FIG. 1.

Referring also to FIG. 2, scattering detector assembly 20 has a disc-shaped central active region 22 and a series of ring-shaped concentric active regions 24, 26, and 28 surrounding central active region 22. Central active region 22 is axially aligned to receive light beam 16 to measure the intensity of portions 16a of light beam 16 that are not scattered and directly impinge on region 22 along axis 17. Ring-shaped concentric active regions 24, 26, and 28 are concentrically disposed about axis 17 and the direction of emitted light beam 16 to measure the light intensity of portions 16b of near-forward scattered light outside of axis 17 and the direction of emitted light beam 16. Only three concentric active regions 24, 26, and 28 made up of segments 24a, 26a, and 28a, respectively are depicted. It is understood that scattering detector assembly 20 of detector 10 can have more or less concentric active regions as desired.

Central active region 22 and arc-shaped segments 24a, 26a, and 28a of ring-shaped concentric active regions 24, 26, and 26 are all connected to a common power supply 30 via leads 30a to provide the same supply voltage to all of the active regions uniformly. This feature permits the photo-gain from central active region 22 and from each of the segments 24a, 26a, and 28a of active regions 22, 24, 26, and 28 to be comparable to each other (i.e. similar in magnitude) or another standard created in interconnected processing system 70. The operating voltage coupled to active regions of scattering detector assembly 20 from power supply 30 is set so that central active region 22 produces a full-scale output signal without saturation when it is illuminated by light beam 16 in air, i.e. interior 14 is filled with air.

Central active region 22 and segments 24a, 26a, and 28a of concentric active regions 24, 26, and 28 may be any suitable photo-detecting active medium, such as photo-conductive components, (photo-diodes). An annular, shallow light baffle 21 can be placed around disc-shaped central detector region 22 to eliminate, or at least reduce surface scatter on the surface of central active region 22 from reaching ring-shaped concentric active regions 24, 26, and 28. The height annular baffle 21a extends above central active region 22 is relatively small, about 1 mm, to avoid interference with the scattering measurement by concentric active regions 24, 26, and 28.

A first annular non-active region 23 of scattering detector assembly 20 is disposed radially outwardly from and adjacent to central active region 22. First annular non-active region 23 surrounds central active region 22 to preclude, or prevent stray light impinging outside the active area of central active region 22 from affecting the reading of impinging light intensity on central active region 22. A second annular non-active region 25 of scattering detector assembly 20 is disposed radially outwardly from and adjacent to concentric active region 24. Second annular non-active region 25 surrounds concentric active region 24 to preclude, or prevent stray light impinging outside the active area of concentric active region 24 from affecting the reading of impinging light intensity on concentric active region 24. A third annular non-active region 27 of scattering detector assembly 20 is disposed radially outwardly from and adjacent to concentric active region 26. Third annular non-active region 27 surrounds concentric active region 26 to preclude stray light impinging outside the active area of concentric active region 26 from affecting the reading of impinging light intensity on concentric active region 26. A fourth annular non-active region 29 of scattering detector assembly 20 is disposed radially outwardly from and adjacent to concentric active region 28. Fourth annular non-active region 29 surrounds concentric active region 28 to preclude stray light impinging outside the active area of concentric active region 28 from affecting the reading of impinging light intensity on concentric active region 28. All the non-active regions are made from materials that do not produce signals in response to impinging light and/or can be or have coatings that absorb light, for example.

Ring-shaped concentric active regions 24, 26, and 26 provide active areas substantially larger than central active region 22. The segments of concentric active regions 24, 26, and 28 can be arranged in any of several fashions in addition to the arrangement of different arc-shaped segments 24a, 26a, 28a of ring-shaped concentric active regions 24, 26, and 28 shown in FIG. 2. However, irrespective of the arrangement, the aggregate of active regions of arc-shaped segments 24a, 26a, and 28a of each of concentric active regions 24, 26, and 28 are made progressively larger in area as their distances from axis 17 of light beam 16 and central active region 22 are made greater, or increased. This progressive increase in areas of concentric active regions 24, 26, and 28 is to accommodate the scattering that diminishes, or falls off rapidly as the distances, or separations increase radially outwardly from axis 17 of light beam 16 in most waters of interest. In other words, the progressive increase of active areas compensates for this fall-off by capturing additional scattered light to enhance signals for effectively use in processing system 70.

Since active regions 22, 24, 26, and 26 are connected to common power supply 30 that provides the same supply voltage to all these regions, the photo-gain from each region is directly comparable. That is, the signal generated by each square mm of active area of active regions 22, 24, 26, and 28, will be the same for the same unit of optical energy that impinges on it. Consequently, impinging light in concentric active region 24 that is the same magnitude as the impinging light that is received in center active region 22 will equate to a specific signal equal to 1 times (area of center active region 22/area of concentric active region 24). If the area ratio between central active region 22 and concentric active region 24 is 1:10, then the comparison signal generated by concentric active region 24 will be 0.1 times the signal generated by central active region 22. While it would obviously be desirable to have the output signal from each of the detection segments similar in magnitude, since the scattering function will vary depending on individual environmental considerations, this can only be approximated in any hardware realization of detector 10. Since the detection process is reasonably linear over at least two orders of magnitude of input signal, the compensation is adequate in most cases.

Detector 10 of this invention provides the ability to measure scattered light in water and compensates for the rapidly decreasing magnitude of the scattered light as concentric active regions are located from the axis and direction of light beam 16. Detector 10 provides the ability to directly compare received signals to obtain a calibrated return (through knowledge of the active areas present), to simultaneously obtain the scattering curve in the entire near-forward scattered region, and uses common supply voltage 30 to ensure commonality in the optical reception process.

Detector 10 can be implemented in several ways without departing from the scope of this invention. Laser 15 and components of scattering detector assembly 20 of detector 10 can be selected from a number of commercially available units that have been appropriately modified to operate successfully in ambient water 40 while undersea tasks are being completed. The size and location of the constituents of scattering detector assembly 20 can be varied, and can be segmented in various ways. Different arrangements of active regions of scattering detector assembly 20 of detector 10 can be used to achieve specific, or different measurement goals. For example, a hemi-circular arrangement of active regions that are rotated in the plane perpendicular to the beam might be used to examine the cylindrical symmetry tacitly assumed in most theoretical models of the ocean optical process. Similarly, in some waters, the photo-detection process may yield signals that are too low for practical use, in which case detector 10 can use avalanche photodiodes in active regions 22, 24, 26, and 28, or other configurations of active regions to improve signal strengths.

Having the teachings of this invention in mind, modifications and alternate embodiments of detector 10 may be adapted. Its uncomplicated, compact design lends itself to numerous modifications to permit its use in the hostile marine environment and on land. For examples, detector 10 can be made larger or smaller in different shapes and fabricated from a wide variety of materials to assure resistance to corrosion, sufficient strength, and long term reliable operation under different operational requirements. Rigid housing member 11 could have different shapes, such as being an elongate rigid member having laser 15 mounted at one end and scattering detector assembly 20 at the other end, and ambient water 40 in-between. Furthermore, concentric active regions 24, 26, and 28 could have different arrangements of differently shaped segments 24a, 26a, and 28a or more or less concentric active regions could be provided. Clamp-like structure or other connective means could be mounted on housing member 14 to allow quick and secure connections to other structural members.

The disclosed components and their arrangements as disclosed herein, all contribute to the novel features of this invention. Detector 10 is a compact, cost-effective, unattended means for measuring scattering and scattering functions on land or underwater. Therefore, detector 10, as disclosed herein is not to be construed as limiting, but rather, is intended to be demonstrative of this inventive concept. It should be readily understood that many modifications and variations of the present invention are possible within the purview of the claimed invention. It is to be understood that within the scope of the appended claims the invention may be practiced otherwise than as specifically described.

I claim:

1. An apparatus for measuring near-forward scattering of ambient water comprising:

a housing member having an interior and elongate openings extending nearly its length between disc-shaped end caps, said elongate openings allowing ambient water to flow freely into and fill said interior extending between said end caps;

a source of light mounted in said interior on one end cap of said housing member to emit a beam of light along an axis extending through water filling said interior; and a scattering detector assembly mounted in said interior on the other end cap of said housing member a predetermined distance from said light source, said detector assembly having a central active region disposed in said axis to receive portions of said beam of light emitted along said axis and a plurality of concentric active regions located radially outwardly from said central active region and said axis to receive scattered portions of said beam of light, said central active region and said concentric active regions providing signals representative of magnitudes of said axial portions and scattered portions of said beam of light.

2. An apparatus according to claim 1 wherein said light source is comprised of a laser, said central active section is a disc-shaped photo-conductive component, said concentric active sections are ring-shaped and are each made from arc-shaped segments of photo-conductive components, and said housing member of said apparatus is adapted to be mounted on a submersible in said ambient water.

3. An apparatus according to claim 2 further comprising:

an annular non-active region surrounding said disc-shaped central active region; and an annular non-active region surrounding each of said ring-shaped concentric active regions.

4. An apparatus according to claim 3 further comprising:
an annular light baffle around and extending above said disc-shaped central active region.

5. An apparatus according to claim 4 wherein said annular non-active region surrounding said disc-shaped central active region prevents stray light impinging on said scattering detector assembly outside of said central active region from affecting the reading of impinging light intensity on said central active region, each annular non-active region surrounding each of said ring-shaped concentric active regions prevents stray light impinging on said scattering detector assembly outside of each ring-shaped concentric active region from affecting the reading of impinging light intensity on each ring-shaped concentric region, and said annular light baffle around and extending above said disc-shaped central detector region reduces surface scatter on the surface of said disc-shaped central active region from reaching said ring-shaped concentric active regions.

6. An apparatus according to claim 5 wherein said ring-shaped concentric active regions are progressively increased in area as their distances from said axis of said light beam and said disc-shaped central active region are increased.

7. An apparatus according to claim 6 wherein said progressive increase in areas of said ring-shaped concentric active regions is to compensate for scattering that diminishes, or falls off rapidly as the distance increases radially outwardly from said axis of said light beam to enhance signals.

8. An apparatus according to claim 1 wherein said light source is comprised of a laser, said central active section is a disc-shaped photo-conductive component, and said concentric active sections are ring-shaped and are each made from arc-shaped segments of avalanche photo diodes to improve strength of signals.

9. A device according to claim 2 further comprising:
means for surrounding said disc-shaped central active section defining means with an annular non-active region; and
means for surrounding each of said plurality of ring-shaped concentric active section defining means with an annular non-active region.

10. A device according to claim 9 further comprising:
means for extending around and above said disc-shaped central active region to provide an annular light baffle.

11. A method of measuring the near-direct forward scattering function in water comprising the steps of:
mounting a source of light and a scattering detector assembly separated a predetermined distance on separate end caps at opposite ends of an interior of a housing member;
filling said interior between said end caps with water from ambient;
emitting a beam of light through the water filled interior from said source of light mounted on one end cap along an axis;
aligning a central active region of said scattering detector assembly on the other end cap with said axis to receive portions of said beam of light emitted through the water filled interior along said axis;
placing a plurality of ring-shaped concentric active regions of said scattering detector assembly radially outwardly from said central active region on the other end cap and said axis to receive scattered portions of said beam of light emitted through the water filled interior; and
providing signals representative of magnitudes of said axially emitted portions and scattered portions of said beam of light.

12. A method according to claim 11 wherein the step of filling includes the steps of:
receiving ambient water in the interior of said housing member through elongate openings extending nearly the length of said housing member;
flooding said interior with said ambient water; and
immersing said light source and said scattering detector assembly in said ambient water in said housing member.

13. A method according to claim 12 further comprising the step of:
coupling said central active region and said concentric active regions to a common power supply in said interior to provide the same supply voltage to all of the active regions uniformly.

14. A method according to claim 13 further comprising the steps of:
surrounding said disc-shaped central active region and said ring-shaped concentric regions with non-active regions.

15. A method according to claim 14 further comprising the steps of:
preventing stray light impinging on said scattering detector assembly outside of said central active region from affecting the reading of impinging light intensity on said central active region by one of said non-active regions; and
preventing stray light impinging on said scattering detector assembly outside of each ring-shaped concentric active region from affecting the reading of impinging light intensity on each ring-shaped concentric region by separate ones of said non-active regions surrounding each of said ring-shaped concentric regions.

16. A method according to claim 15 further comprising the step of:
extending an annular light baffle around and above said disc-shaped central active region.

17. A method according to claim 16 further comprising the step of:
reducing surface scatter on the surface of said disc-shaped central active region from reaching said ring-shaped concentric active regions by said annular light baffle.

18. A method according to claim 17 further comprising the step of:
progressively increasing the areas of said ring-shaped concentric active regions as their distances from said axis of said light beam and said disc-shaped central active region are increased.

19. A method according to claim 18 wherein said step of progressively increasing includes the step of:
compensating for scattering of light that diminishes, or falls off rapidly as the distance increases radially outwardly from said axis of said light beam to enhance signals.

20. A device to measure near-forward scattering function of water comprising:
means for providing a housing member having an interior and elongate openings extending nearly its length between disc-shaped end caps, said elongate openings allowing ambient water to flow freely into and fill said interior extending between said end caps;
means mounted on said housing member providing means in said interior on one end cap for emitting a beam of light along an axis extending through water filling said interior; and means mounted in said interior on the other end cap of said housing member providing means spaced from said emitting means for detecting light, said light detecting means having a means defining a central active region disposed in said axis to receive portions of said beam of light emitted along said axis and a plurality of means for defining concentric active regions located radially outwardly from said central active region defining means and said axis to receive scattered portions of said beam of light, said central active region defining means and said plurality of concentric active region defining means providing signals representative of magnitudes of said axial portions and scattered portions of said beam of light.

21. A device according to claim 20 wherein said light source is comprised of a laser, said central active section defining means is a disc-shaped photo-conductive component, and said plurality of concentric active section defining means are ring-shaped and are each made from arc-shaped segments of photo-conductive components, and said housing member providing means of said apparatus is adapted to be mounted on a submersible in said ambient water.

* * * * *